US005744509A

United States Patent [19]
Wilson et al.

[11] Patent Number: 5,744,509
[45] Date of Patent: Apr. 28, 1998

[54] FOAMED POLYMER AND PROCESS FOR PRODUCTION THEREOF

[75] Inventors: Robert N. Wilson, Hixson, Tenn.; G. Ronald Blair, Richmond Hill, Canada

[73] Assignee: Woodbridge Foam Corporation, Canada

[21] Appl. No.: 674,190

[22] Filed: Jul. 1, 1996

[51] Int. Cl.$^6$ .............................. C08J 9/04; C08G 18/02
[52] U.S. Cl. .............................. 521/125; 521/52; 521/99; 521/109.1; 521/134; 521/137; 521/139; 521/155; 521/163; 521/170; 521/172
[58] Field of Search .................... 521/52, 99, 109.1, 521/125, 134, 137, 139, 155, 163, 170, 172, 174, 905

[56] References Cited

U.S. PATENT DOCUMENTS

| | | | |
|---|---|---|---|
| 3,171,820 | 3/1965 | Volz . | |
| 3,175,025 | 3/1965 | Geen et al. . | |
| 3,781,231 | 12/1973 | Janssen et al. . | |
| 3,799,898 | 3/1974 | Lamplugh et al. . | |
| 3,900,030 | 8/1975 | Bashan . | |
| 4,062,817 | 12/1977 | Westerman . | |
| 4,066,583 | 1/1978 | Spaulding . | |
| 4,167,464 | 9/1979 | George . | |
| 4,190,562 | 2/1980 | Westerman . | |
| 4,259,452 | 3/1981 | Yukuta et al. | 521/914 |
| 4,394,930 | 7/1983 | Korpman . | |
| 4,466,993 | 8/1984 | Hou et al. . | |
| 4,486,489 | 12/1984 | George | 428/220 |
| 4,699,619 | 10/1987 | Bernardin | 604/378 |
| 4,715,918 | 12/1987 | Lang | 156/273.1 |
| 4,725,629 | 2/1988 | Garvey et al. | 521/137 |
| 4,731,391 | 3/1988 | Garvey | 521/137 |
| 4,775,375 | 10/1988 | Aledo | 604/378 |
| 4,798,876 | 1/1989 | Gould et al. | 525/457 |
| 4,810,582 | 3/1989 | Gould et al. | 428/423.1 |
| 4,960,477 | 10/1990 | Mesek | 156/209 |
| 4,977,892 | 12/1990 | Ewall . | |
| 4,985,467 | 1/1991 | Kelly et al. | 521/109.1 |
| 5,009,650 | 4/1991 | Bernardin | 604/378 |
| 5,098,423 | 3/1992 | Pieniak et al. | 604/385.1 |
| 5,176,668 | 1/1993 | Bernardin | 604/368 |
| 5,185,009 | 2/1993 | Sitnam | 604/364 |
| 5,188,624 | 2/1993 | Young, Sr. et al. | 604/378 |
| 5,188,626 | 2/1993 | Toyoda et al. | 604/385.1 |
| 5,219,342 | 6/1993 | Hatch et al. | 604/386.1 |
| 5,246,431 | 9/1993 | Minetola et al. | 604/385.2 |
| 5,257,982 | 11/1993 | Cohen et al. | 604/378 |
| 5,261,900 | 11/1993 | Houle et al. | 604/385.1 |
| 5,263,948 | 11/1993 | Karami et al. | 604/383 |
| 5,263,949 | 11/1993 | Karami et al. | 604/383 |
| 5,275,590 | 1/1994 | Huffman et al. | 604/385.2 |
| 5,300,054 | 4/1994 | Feist et al. | 604/378 |
| 5,304,161 | 4/1994 | Noel et al. | 604/378 |
| 5,328,935 | 7/1994 | Van Phan et al. | 521/150 |
| 5,330,457 | 7/1994 | Cohen | 604/378 |
| 5,334,177 | 8/1994 | Cohen | 604/378 |
| 5,336,695 | 8/1994 | Nass et al. | 521/137 |
| 5,338,766 | 8/1994 | Phan et al. | 521/149 |
| 5,342,344 | 8/1994 | Lancaster et al. | 604/387 |
| 5,370,634 | 12/1994 | Ando et al. | 604/385.1 |
| 5,401,266 | 3/1995 | Runeman et al. | 604/378 |
| 5,439,458 | 8/1995 | Noel et al. | 604/378 |
| 5,447,508 | 9/1995 | Numano et al. | 604/385.2 |
| 5,462,541 | 10/1995 | Bruemmer et al. | 604/391 |
| 5,486,167 | 1/1996 | Dragoo et al. | 604/384 |
| 5,531,727 | 7/1996 | Cohen et al. | 604/378 |
| 5,591,779 | 1/1997 | Bleys et al. | 521/137 |

FOREIGN PATENT DOCUMENTS

| | | |
|---|---|---|
| 1207486 | 7/1986 | Canada . |
| 1250190 | 2/1989 | Canada . |
| 0288865 | 11/1991 | European Pat. Off. . |
| 4233289 | 4/1994 | Germany . |
| 4308347 | 9/1994 | Germany . |
| 5792032 | 6/1982 | Japan . |
| 1317930 | 5/1973 | United Kingdom . |
| 1354576 | 5/1974 | United Kingdom . |

*Primary Examiner*—John M. Cooney, Jr.
*Attorney, Agent, or Firm*—Fitzpatrick, Cella, Harper & Scinto

[57] ABSTRACT

A foamed isocyanate-based polymer having a cellular structure and comprising a superabsorbent material, the polymer being capable of: (i) absorbing at least about 10 times its weight of a 0.9 wt./wt. % aqueous NaCl solution maintained at a temperature of from about 20° to about 25° C., and (ii) retaining at least about 10 times its weight of absorbed aqueous NaCl solution which is bound to the superabsorbent material, the cellular structure having a cell size of at least about 30 cells/inch when measured pursuant to ASTM D3576-77. A process for producing the foamed isocyanate-based polymer is also described. The process comprises the steps of: contacting an isocyanate, an active hydrogen-containing compound, an aqueous blowing agent, a catalyst and a superabsorbent material, the superabsorbent material being capable of absorbing at least about 10 times its weight of a 0.9 wt./wt. % aqueous NaCl solution maintained at a temperature in the range of from about 20° to about 25° C.; and expanding the reaction mixture to produce the foamed isocyanate-based polymer. The active hydrogen-containing compound comprises from about 10% to 100% by weight of a hydrophilic active hydrogen-containing compound and from 0 to about 90% by weight a non-hydrophilic active hydrogen-containing compound. The foamed isocyanate-based polymer is ideally suitable for use in an absorption layer in a personal hygiene device.

33 Claims, No Drawings

FOAMED POLYMER AND PROCESS FOR PRODUCTION THEREOF

BACKGROUND OF THE INVENTION

1. Field of the Invention

The present invention relates to a foamed polymer and to a process for production thereof. More particularly, the present invention relates to a foamed isocyanate-based polymer (e.g. polyurethane foam, polyurea foam, polyisocyanurate foam, etc.) and a process for production thereof.

2. Description of the Prior Art

Isocyanate-based polymers are known in the art. Generally, those of skill in the art understand isocyanate-based polymers to be polyurethanes, polyureas, polyisocyanurates and mixtures thereof.

It is also known in the art to produce foamed isocyanate-based polymers. Indeed, one of the advantages of isocyanate-based polymers compared to other polymer systems is that the chemistry can be used to achieve desired product properties in situ.

One of the conventional ways to produce a polyurethane foam is known as the "one-shot" technique. In this technique, the isocyanate, a suitable polyol, a catalyst, water (which acts to generate carbon dioxide as the blowing agent and can optionally be supplemented with one or more secondary organic blowing agents) and other additives are mixed together at once using, for example, a mechanical or impingement mixer. Generally, if one were to produce a polyurea, the polyol would be replaced with a suitable polyamine. A polyisocyanurate may result from cyclotrimerization of the isocyanate component. Urethane-modified polyureas or polyisocyanurates are known in the art. In either scenario, the reactants would be intimately mixed quickly using a suitable mixer.

Another technique for producing foamed isocyanate-based polymers is known as the "prepolymer" technique. In this technique, a prepolymer of polyol and isocyanate (in the case of a polyurethane) are reacted in an inert atmosphere to form a liquid polymer terminated with isocyanate groups. To produce the foamed polymer, the prepolymer is thoroughly mixed with water and, optionally, a polyol (in the case of producing a polyurethane) or a polyamine (in the case of producing a polyurea) in the presence of a catalyst or a cross-linker. Alternatively, the prepolymer could be a liquid polymer terminated with hydroxyl groups which would then be reacted with isocyanate in the presence of a catalyst or a cross-linker to produce the foam.

As is known by those of skill in the art, many conventional isocyanate-based foams are non-hydrophilic (i.e. relatively hydrophobic). Such foams generally have an aversion to aqueous fluids. Practically, this results in such foams being unable to absorb or pick up significant quantities of aqueous fluids (e.g. the foams will float on water) other than by mechanical entrainment. Accordingly, such foams are virtually never used in an application in which significant aqueous fluid absorption and retention is a desired feature.

In copending U.S. patent application Ser. Nos. 08/413,433 (Wilson) and 08/554,896 (Wilson), the contents of each of which are hereby incorporated by reference, there is disclosed a foamed isocyanate-based polymer having a cellular structure and containing a superabsorbent material, the polymer being capable of: (i) absorbing at least about 20 times its weight of an aqueous fluid maintained at a temperature of from about 20° to about 25° C., and (ii) retaining at least about 20 times its weight of absorbed aqueous fluid which is bound to the superabsorbent material. The foamed isocyanate-based polymer disclosed in the Wilson No. '433 and No. '896 applications may be produced by a process which comprises reacting and expanding (via a suitable catalyst and blowing agent) a mixture comprising an isocyanate, an active hydrogen-containing compound and a superabsorbent material. The superabsorbent material is capable of absorbing at least about 20 times its weight of an aqueous fluid maintained at a temperature in the range of from about 20° to about 25° C. The active hydrogen-containing compound comprises from about 10% to 100% by weight of a hydrophilic active hydrogen-containing compound and from 0 to about 90% by weight a non-hydrophilic active hydrogen-containing compound. The foamed isocyanate-based polymer is ideally suitable for use in an absorption layer in a personal hygiene device.

While the foamed isocyanate-based polymer disclosed in the Wilson No. '433 and No. '896 applications represents a significant advance in the art, there is continuous need for improvements in the art. For example, there is a continuous need to improve and optimize the fluid absorbing efficiency of the superabsorbent material contained in the foam matrix. Depending on the particular application for the foamed polymer, such an improvement would allow either: (i) reduction of the amount of superabsorbent material required to meet a specified fluid absorption/retention (thereby reducing the cost of producing the foamed polymer), or (ii) the ability to improve the performance of the foamed polymer (i.e. increasing the fluid absorption/retention thereof) beyond that conventionally obtained.

In light of the above, it would be advantageous to have a foamed isocyanate-based polymer which is hydrophilic and characterized by improved absorption (or pick up) and retention of an aqueous fluid. It would be further advantageous if such a foam could be produced in a relatively uncomplicated way and possessed reproducible physical properties.

SUMMARY OF THE INVENTION

It is an object of the present invention to provide a novel foamed isocyanate-based polymer having improved aqueous fluid absorption and retention properties.

It is an object of the present invention to provide a novel process for producing such a foamed isocyanate-based polymer.

It is another object of the present invention to provide a novel personal hygiene device incorporating such a foamed isocyanate-based polymer.

Accordingly, in one of its aspects, the present invention provides a foamed isocyanate-based polymer having a cellular structure and comprising a superabsorbent material, the polymer being capable of: (i) absorbing at least about 10 times its weight of a 0.9 wt./wt. % aqueous NaCl solution maintained at a temperature of from about 20° to about 25° C., and (ii) retaining at least about 10 times its weight of absorbed aqueous NaCl solution which is bound to the superabsorbent material, the cellular structure having a cell size of at least about 30 cells/inch when measured pursuant to ASTM D3576-77.

In another of its aspects, the present invention provides a foamed polyurethane polymer comprising poly(acrylic acid alkali metal salt) in an amount in the range of from about 10 to about 65 parts by weight per hundred parts by weight of polyol used to produce the foamed polyurethane polymer, the polymer being capable of: (i) absorbing from about 10 to about 20 times its weight of a 0.9 wt./wt. % aqueous NaCl solution maintained at a temperature of from about 20° to about 25° C., and (ii) retaining from about 10 to about 20 times its weight of absorbed aqueous NaCl solution which is bound to the poly(acrylic acid alkali metal salt), the cellular structure having a cell size of at least about 30 cells/inch when measured pursuant to ASTM D3576-77.

In yet another of its aspects, the present invention provides a process for producing a foamed isocyanate-based polymer comprising the steps of:

providing a substantially uniform mixture comprising an isocyanate, an active hydrogen-containing compound and a superabsorbent material, the superabsorbent material being capable of absorbing at least about 10 times its weight of a 0.9 wt./wt. % aqueous NaCl solution maintained at a temperature in the range of from about 20° to about 25° C.;

adding to the substantially uniform mixture an aqueous blowing agent and a catalyst to form a reaction mixture; and expanding the reaction mixture to produce the foamed isocyanate-based polymer;

wherein the active hydrogen-containing compound comprises from about 10% to 100% by weight of a hydrophilic active hydrogen-containing compound and from 0 to about 90% by weight a non-hydrophilic active hydrogen-containing compound.

In an alternate embodiment of the present process, a process is provided for producing a foamed isocyanate-based polymer comprising the steps of:

providing a substantially uniform mixture comprising an aqueous blowing agent, a catalyst, an active hydrogen-containing compound and a superabsorbent material, the superabsorbent material being capable of absorbing at least about 10 times its weight of a 0.9 wt./wt. % NaCl solution maintained at a temperature in the range of from about 20° to about 25° C.;

adding to the substantially uniform mixture an isocyanate to form a reaction mixture; and expanding the reaction mixture to produce the foamed isocyanate-based polymer;

wherein the active hydrogen-containing compound comprises from about 10% to 100% by weight of a hydrophilic active hydrogen-containing compound and from 0 to about 90% by weight a non-hydrophilic active hydrogen-containing compound.

In a further alternate embodiment of the present process, a process is provided for producing a foamed isocyanate-based polymer comprising the steps of:

providing a dispersion comprising a substantially uniform mixture of an active hydrogen-containing compound and a superabsorbent material, the superabsorbent material being capable of absorbing at least about 10 times its weight of a 0.9 wt./wt. % aqueous NaCl solution maintained at a temperature in the range of from about 20° to about 25° C.;

contacting the dispersion with an isocyanate, a catalyst and an aqueous blowing agent to form a reaction mixture; and expanding the reaction mixture to produce the foamed isocyanate-based polymer;

wherein the active hydrogen-containing compound comprises from about 10% to 100% by weight of a hydrophilic active hydrogen-containing compound and from 0 to about 90% by weight a non-hydrophilic active hydrogen-containing compound.

When any of the embodiments of the process are used to prepare a foamed polyurethane or a foamed urea-modified polyurethane, it is possible, and indeed preferred, to use a single polyol or a mixture of polyols which possesses an overall ethylene oxide content in the range of from about 15 to about 80, preferably from about 20 to about 70, more preferably from about 35 to about 70, most preferably from about 50 to about 65, percent by weight, the remainder comprised of other polyoxyalkylene groups such as propylene oxide, butylene oxide or mixtures thereof.

In yet another of its aspects, the present invention provides a personal hygiene device having a bodily fluid absorbent layer consisting essentially of a foamed isocyanate-based polymer having a cellular structure and comprising a superabsorbent material, the polymer being capable of: (i) absorbing at least about 10 times its weight of a 0.9 wt./wt. % aqueous NaCl solution maintained at a temperature of from about 20° to about 25° C., and (ii) retaining at least about 10 times its weight of absorbed NaCl solution which is bound to the superabsorbent material, the cellular structure having a cell size of at least about 30 cells/inch when measured pursuant to ASTM D3576-77.

As used throughout this specification, the term "isocyanate-based polymer" is intended to mean, inter alia, polyurethane, polyurea and polyisocyanurate. Further, the terms "0.9 wt./wt. % aqueous NaCl solution" and "saline solution" are used interchangeably through this specification and are intended to have the same meaning.

The cellular structure of the present foamed isocyanate-based polymer has a cell size of at least about 30 cells/inch when measured pursuant to ASTM D3576-77. Those of skill in art will recognize that is equivalent to a cell size of at least about 1/30 inch, at least about 1.18 cells/mm or at least about 0.847 mm. Thus, while the unit cells/inch is used hereinbelow, conversion to these other units should be considered supported in this specification.

DETAILED DESCRIPTION OF THE PREFERRED EMBODIMENTS

Thus, the present inventors have surprisingly and unexpectedly discovered that the use of a relatively fine cellular structure, in combination with a superabsorbent material, improves 0.9 wt./wt. % aqueous NaCl solution absorption and retention properties of the foamed polymer described in the Wilson No. '433 and No. '896 applications referred to hereinabove. Specifically, the present inventors have discover that the combination of a foamed isocyanate-based polymer with a cellular matrix having a cell size of at least about 30 cells/inch when measured pursuant to ASTM D3576-77 with a superabsorbent material. Preferably, the cell size of the cellular matrix is in the range of from about 30 to about 80, more preferably from about 30 to about 60, most preferably from about 30 to about 45, cells/inch when measured pursuant to ASTM D3576-77.

In a particularly preferred embodiment of the present foamed isocyanate-based polymer, the superabsorbent material has a particle size of at least about 400 µm. This additional feature has been found to further enhance the absorption and retention properties of the foamed polymer described in the Wilson '433 and '896 applications referred to hereinabove. As used throughout this specification, the term "particle size" is intended to have a broad meaning and relates to the largest dimension of the particles of superabsorbent material. Thus, the superabsorbent materials useful in the present invention include particles (substantially spherical or irregular shaped), flakes and fibers.

The present invention relate to, inter alia, a foamed isocyanate-based polymer comprising a superabsorbent material and to a process for production thereof. Generally, the present foamed isocyanate-based polymer is selected from the group comprising polyurethane foam, polyurea foam, polyisocyanurate foam, urea-modified polyurethane foam, urethane-modified polyurea foam, urethane-modified polyisocyanurate foam and urea-modified polyisocyanurate foam. The preferred foamed isocyanate-based polymer is selected from the group consisting of polyurethane foam and urea-modified polyurethane foam. The most preferred isocyanate-based polymer is polyurethane foam. As is known in the art, the term "modified", when used in conjunction with a polyurethane, polyurea or polyisocyanurate means that up to 50% of the polymer backbone forming linkages have been substituted.

Each embodiment of the present process comprises reacting and expanding (via a suitable catalyst and blowing agent) a mixture comprising an isocyanate, an active hydrogen-containing compound and a superabsorbent material. The superabsorbent material preferably has a particle size of at least 400 μm and is capable of absorbing at least about 10 times its weight of 0.9 wt./wt. % aqueous NaCl solution maintained at a temperature in the range of from about 20° to about 25° C. The active hydrogen-containing compound comprises from about 10% to 100% by weight of a hydrophilic active hydrogen-containing compound and from 0 to about 90% by weight a non-hydrophilic active hydrogen-containing compound.

The isocyanate suitable for use in the substantially uniform mixture is not particularly restricted and the choice thereof is within the purview of a person skilled in the art. Generally, the isocyanate compound suitable for use may be represented by the general formula:

Q(NCO)$_i$ wherein i is an integer of two or more and Q is an organic radical having the valence of i. Q may be a substituted or unsubstituted hydrocarbon group (e.g. an alkylene or arylene group). Moreover, Q may be represented by the general formula:

Q$^1$—Z—Q$^1$ wherein Q$^1$ is an alkylene or arylene group and Z is chosen from the group comprising —O—, —O—Q$^1$—, —CO—, —S—, —S—Q$^1$—S— and —SO$_2$—. Examples of isocyanate compounds which fall within the scope of this definition include hexamethylene diisocyanate, 1,8-diisocyanato-p-methane, xylyl diisocyanate, (OCNCH$_2$CH$_2$CH$_2$OCH$_2$O)$_2$, 1-methyl-2,4-diisocyanatocyclohexane, phenylene diisocyanates, toluene diisocyanates, chlorophenylene diisocyanates, diphenylmethane4,4'-diisocyanate, naphthalene-1,5-diisocyanate, triphenylmethane-4,4',4"-triisocyanate and isopropylbenzene-alpha-4-diisocyanate.

In another embodiment, Q may also represent a polyurethane radical having a valence of i. In this case Q(NCO)$_i$ is a compound which is commonly referred to in the art as a prepolymer. Generally, a prepolymer may be prepared by reacting a stoichiometric excess of an isocyanate compound (as defined hereinabove) with an active hydrogen-containing compound (as defined hereinafter), preferably the polyhydroxyl-containing materials or polyols described below. In this embodiment, the polyisocyanate may be, for example, used in proportions of from about 30 percent to about 200 percent stoichiometric excess with respect to the proportion of hydroxyl in the polyol. The prepolymer may then be reacted with a polyol (not always required), aqueous blowing agent (water), catalyst and, optionally, other additives, to produce a polyurethane foam or an amine to produce a polyurea-modified polyurethane.

In another embodiment, the isocyanate compound suitable for use in the process of the present invention may be selected from dimers and trimers of isocyanates and diisocyanates, and from polymeric diisocyanates having the general formula:

[Q"(NCO)$_i$]$_j$ wherein both i and j are integers having a value of 2 or more, and Q" is a polyfunctional organic radical, and/or, as additional components in the reaction mixture, compounds having the general formula:

L(NCO)$_i$ wherein i is an integer having a value of 1 or more and L is a monofunctional or polyfunctional atom or radical. Examples of isocyanate compounds which fall with the scope of this definition include ethylphosphonic diisocyanate, phenylphosphonic diisocyanate, compounds which contain a =Si—NCO group, isocyanate compounds derived from sulfonamides (QSO$_2$NCO), cyanic acid and thiocyanic acid.

See also for example, British patent No. 1,453,258, the contents of which are incorporated herein by reference.

Non-limiting examples of suitable isocyanates include: 1,6-hexamethylene diisocyanate, 1,4-butylene diisocyanate, furfurylidene diisocyanate, 2,4-toluene diisocyanate, 2,6-toluene diisocyanate, 2,4'-diphenylmethane diisocyanate, 4,4'-diphenylmethane diisocyanate, 4,4'-diphenylpropane diisocyanate, 4,4'-diphenyl-3,3'-dimethyl methane diisocyanate, 1,5-naphthalene diisocyanate, 1-methyl-2,4-diisocyanate-5-chlorobenzene, 2,4-diisocyanato-s-triazine, 1-methyl-2,4-diisocyanato cyclohexane, p-phenylene diisocyanate, m-phenylene diisocyanate, 1,4-naphthalene diisocyanate, dianisidine diisocyanate, bitoluene diisocyanate, 1,4-xylylene diisocyanate, 1,3-xylylene diisocyanate, bis-(4-isocyanatophenyl)methane, bis-(3-methyl4-isocyanatophenyl)methane, polymethylene polyphenyl polyisocyanates and mixtures thereof. A more preferred isocyanate is selected from the group comprising 2,4'-diphenylmethane diisocyanate, 4,4'-diphenylmethane diisocyanate and mixtures thereof, for example, a mixture comprising from about 15 to about 25 percent by weight 2,4'-diphenylmethane diisocyanate and from about 75 to about 85 percent by weight 4,4'-diphenylmethane diisocyanate. An example of such an isocyanate is commercially available from Imperial Chemical Industries under the tradename Rubinate M and from The Dow Chemical Company under the tradename PAPI 4027. The most preferred isocyanate is selected from the group comprising 2,4-toluene diisocyanate, 2,6-toluene diisocyanate and mixtures thereof, for example, a mixture comprising from about 75 to about 85 percent by weight 2,4-toluene diisocyanate and from about 15 to about 25 percent by weight 2,6-toluene diisocyanate. An example of such an isocyanate is commercially available from The Dow Chemical Company under the tradename Voranate T80.

The active hydrogen-containing compound used in the uniform mixture comprises from about 10% to 100% by weight of a hydrophilic active hydrogen-containing compound and from 0 to about 90% by weight a non-hydrophilic active hydrogen-containing compound. Preferably, the active hydrogen-containing compound comprises from about 20% to about 90%, more preferably from about 40% to about 90%, most preferably from about 60% to about 80%, by weight of a hydrophilic active hydrogen-containing compound and from about 10% to about 80%, more preferably from about 10% to about 60%, most preferably from about 20% to about 30%, by weight a non-hydrophilic active hydrogen-containing compound.

Preferably, the hydrophilic active hydrogen-containing compound is a hydrophilic polyol. As is known in the term "hydrophilic polyol" is intended to mean a polyol which confers hydrophilicity to the foam product. Ideally the hydrophilic polyol has a molecular weight in the range of from about 1500 to about 6000. Preferably, the hydrophilic polyol is selected from the group consisting of diols, triols, tetrols and mixtures thereof, each of which contain polyoxyalkylene groups, the polyoxyalkylene groups comprising at least about 25, more preferably from about 40 to about 85, most preferably from about 55 to about 85, percent by weight of ethylene oxide. As is known in the art, the balance of the polyoxyalkylene groups is conventionally made up of one or both of propylene oxide and butylene oxide, preferably solely propylene oxide. A particularly preferred hydrophilic polyol is commercially available from Arco Chemical Company under the tradename Arcol 2580. Another preferred hydrophilic polyol is commercially available from The Dow Chemical Company under the tradename Voranol CP1421. Yet another preferred hydrophilic polyol is commercially available from BASF Corporation under the tradename Pluracol 593.

Alternatively, if it is desired to produce a polyurea, the active hydrogen-containing compound may be derived from a hydrophilic polyol as described above which as been reacted or capped with an amine. Such amination is within the purview of a person skilled in the art.

The non-hydrophilic active hydrogen-containing compound, if present, is selected from the group consisting of non-hydrophilic polyols, polyamines, polyamides, polyimines, polyolamines and mixtures thereof.

If the process is utilized to produce a polyurethane foam, the non-hydrophilic active hydrogen-containing compound is typically a non-hydrophilic polyol. Generally, if such non-hydrophilic polyols contain or are based on ethylene oxide, the ethylene oxide will be present in amounts of less than about 20% by weight. The choice of such a polyol is not particularly restricted and is within the purview of a person skilled in the art. For example, the polyol may be a hydroxyl-terminated compound selected from the group comprising polyether, polyester, polycarbonate, polydiene and polycaprolactone. The polyol may be selected from the group comprising hydroxyl-terminated polyhydrocarbons, hydroxyl-terminated polyformals, fatty acid triglycerides, hydroxyl-terminated polyesters, hydroxymethyl-terminated polyesters, hydroxymethyl-terminated perfluoromethylenes, polyalkylene ether glycols, polyalkylenearyleneether glycols and polyalkyleneether triols. The polyol may also be selected from the group comprising adipic acid-ethylene glycol polyester, poly(butylene glycol), poly(propylene glycol) and hydroxyl-terminated polybutadiene—see, for example, British patent No. 1,482,213, the contents of which are incorporated herein by reference. Preferably, such a polyol has a molecular weight in the range of from about 200 to about 20,000, more preferably from about 1,500 to about 4,300, most preferably from about 2,500 to about 3,500. Ideally, such a polyol would contain predominantly secondary hydroxyl groups.

As discussed above, it is possible to utilize a prepolymer technique to produce a polyurethane foam within the scope of the present invention. In one embodiment, it is contemplated that the prepolymer be prepared by reacting an excess of isocyanate with a hydrophilic polyol (as discussed above). The prepolymer could then be reacted with a non-hydrophilic polyol (as discussed above) to produce a polyurethane foam or an amine to produce a polyurea-modified polyurethane. In another embodiment, it is contemplated that the prepolymer be prepared by reacting an excess of isocyanate with a non-hydrophilic polyol (as discussed above). The prepolymer could then be reacted with a hydrophilic polyol (as discussed above) to produce a polyurethane foam. In yet another embodiment, if a single polyol provides a desirable overall ethylene oxide content (as discussed above), the prepolymer can be prepared and reacted to produce polyurethane using the same polyol.

If the process is utilized to produce a polyurea-modified polyurethane foam, the non-hydrophilic active hydrogen-containing compound comprises, at least in part, compounds wherein hydrogen is bonded to nitrogen. Preferably such compounds are selected from the group comprising polyamines, polyamides, polyimines and polyolamines, more preferably polyamines. Non-limiting examples of such compounds include primary and secondary amine terminated polyethers. Preferably such polyethers have a molecular weight of greater than about 1500, a functionality of from 2 to 6, and an amine equivalent weight of from about 200 to about 6,000. Such amine terminated polyethers are typically made from an appropriate initiator to which a lower alkylene (e.g. ethylene, propylene, butylene and mixtures thereof) oxide is added with the resulting hydroxyl terminated polyol being subsequently aminated. If two or more alkylene oxides are used, they may be present either as random mixtures or as blocks of one or the other polyether. For ease of amination, it is especially preferred that the hydroxyl groups of the polyol be essentially all secondary hydroxyl groups. Typically, the amination step replaces the majority but not all of the hydroxyl groups of the polyol.

If the process is used to produce a polyurethane foam or a urea-modified polyurethane, it is possible, and indeed preferred, to use a single polyol or a mixture of polyols which possesses an overall ethylene oxide content in the range of from about 15 to about 80, preferably from about 20 to about 70, more preferably from about 35 to about 70 most preferably from about 50 to about 65, percent by weight, the remainder comprised of other polyoxyalkylene groups such as propylene oxide, butylene oxide or mixtures thereof. While a preferred and practical method of achieving such an overall ethylene oxide content is by blending a hydrophilic polyol and a non-hydrophilic polyol as described hereinabove, it will be appreciated that it is possible and likely even preferred to use a single polyol which possesses substantially the same ethylene oxide content as a mixture of a hydrophilic polyol and a non-hydrophilic polyol. Such a polyol is disclosed in copending U.S. patent application Ser. No. 08/576,695, filed Dec. 21, 1995, the contents of which are hereby incorporated by reference.

The superabsorbent material used in the present invention is capable of absorbing at least about 10 times its weight of a 0.9 wt./wt. % aqueous NaCl solution maintained at a temperature in the range of from about 20° to about 25° C. Preferably, the superabsorbent material is a synthetic polymer such as a cellulosic polymer or a polymer of at least one of an acrylic monomer and vinyl monomer, although it is possible to use other materials such as copolymers of maleic acid and isobutylene (typically in fiber form), cross-linked polyethylene oxide and polyethers. A non-limiting example of a suitable cellulosic polymer is a carboxymethyl cellulose and alkali metal salts thereof. A non-limiting example of a suitable polymer of at least one of an acrylic monomer and vinyl monomer may be selected from the group consisting of polyvinylpyrrolidone, sulfonated polystyrene, polysulfethyl acrylate, poly(2-hydroxyethylacrylate), polyacrylamide, poly(acrylic acid) and alkali metal salts thereof, poly(acrylic acid alkali metal salt), starch modified polyacrylic acid and alkali metal salts thereof, poly(starch modified acrylic acid alkali metal salt), hydrolyzed polyacrylonitrile and alkali metal salts thereof, poly(hydrolyzed polyacrylonitrile alkali metal salt), poly(vinyl alcohol acrylic acid alkali metal salt), salts thereof and mixtures thereof. Most preferably, the superabsorbent material is a poly(acrylic acid alkali metal salt) such as poly(sodium acrylate).

Preferably, the superabsorbent material has a particle size of at least about 250 μm, more preferably in the range of from about 250 μm to about 850 μm, even more preferably in the range of from about 400 μm to about 850 μm, most prferably in the range of from about 400 μm to about 750 μm.

While the amount of superabsorbent material used in the present process is not particularly restricted, it is preferred that the superabsorbent material be present in an amount up to about 150 parts by weight per hundred parts by weight of active hydrogen-containing compound used to produce the foamed isocyanate-based polymer. More preferably, the superabsorbent material is present in an amount in the range of from about 20 to about 80 parts, even more preferably from about 25 to about 75, most preferably from about 30 to about 65, by weight per hundred parts by weight of active hydrogen-containing compound used to produce the foamed isocyanate-based polymer. Of course, as improvements are made to superabsorbent materials, it is contemplated that the loading level required in the present foamed isocyanate-based polymer may be reduced while maintaining a given absorption and retention.

As is known in the art, aqueous blowing agents such as water can be used as a reactive blowing agent in the production of foamed isocyanate-based polymers. Specifically, water reacts with the isocyanate forming carbon dioxide which acts as the effective blowing agent in the final foamed polymer product. Optionally, organic blowing agents may be used in conjunction with the aqueous blowing agent, although the use of such blowing agents is generally being curtailed for environmental considerations. It is known in the art that the amount of water used as a blowing agent in the preparation of a foamed isocyanate-based polymer is conventionally in the range of from about 0.5 to as high as about 20 or more parts by weight, preferably from about 1.0 to about 5.0 parts by weight, based on 100 parts by weight of the total active hydrogen-containing compound content in the reaction mixture. Since the amount of water used in the production of a foamed isocyanate-based polymer is limited by the fixed properties expected in the foamed polymer, it may be necessary, in certain circumstances, to utilize a substantially inert liquid extenders when high loadings of filler material are contemplated. Non-limiting examples of suitable liquid extenders include halogenated hydrocarbons and high molecular weight hydrocarbons.

The catalyst added to the uniform mixture of isocyanate, active hydrogen-containing compound and superabsorbent material is a compound capable of catalyzing the polymerization reaction. Such catalysts are known, and the choice and concentration thereof is within the purview of a person skilled in the art. See for example U.S. Pat. Nos. 4,296,213 and 4,518,778, the contents of each of which is incorporated herein by reference. Non-limiting examples of suitable catalysts include tertiary amines and/or organometallic compounds. Additionally, as is known in the art, when the objective is to produce an isocyanurate, a Lewis acid must be used as the catalyst, either alone or in conjunction with other catalysts. Of course it will be understood by those skilled in the art that a combination of two or more catalysts may be suitably used.

In one embodiment of the present process, an initial step comprises the formation of a uniform mixture comprising the isocyanate, the active hydrogen-containing compound and the superabsorbent material. The manner by which the uniform mixture is prepared is not particularly restricted. Thus, it is possible to preblend the components in a separate tank which is then connected to a suitable mixing device for mixing with the aqueous blowing agent and catalyst. The aqueous blowing agent and catalyst may be fed to the mixing device independently or as a mixture.

In another embodiment of the present process, an initial step comprises the formation of a uniform mixture comprising the aqueous blowing agent, the active hydrogen-containing compound, the catalyst and the superabsorbent material. The manner by which the uniform mixture is prepared is not particularly restricted. Thus, it is possible to preblend the components in a separate tank which is then connected to a suitable mixing device for mixing with the isocyanate. The isocyanate may be fed to the mixing device in a conventional manner.

In yet another embodiment of the present process, an initial step comprises the provision of a preblend of the superabsorbent material with the active hydrogen-containing compound. This preblend could then be fed to a suitable mixhead which would also receive independent streams of the isocyanate, the aqueous blowing agent and the catalyst. Alternatively, the aqueous blowing agent and catalyst streams could be combined prior to the mixhead, if desired. In this embodiment, care would have to be taken to design the mixhead to ensure that the preblend and isocyanate streams are adequately mixed at the time that the aqueous blowing agent and catalyst stream(s) are added.

As will be clearly understood by those of skill in the art, it is contemplated that conventional additives in the isocyanate-based polymer art be used in the process. Non-limiting examples of such additives include: surfactants (e.g. organo-silicone compounds available under the tradename L-5770 from OSi), cell openers (e.g. silicone oils), extenders (e.g. halogenated paraffins commercially available as Cereclor S45 from ICI plc), cross-linkers (e.g. low molecular weight reactive hydrogen-containing compositions), pigments/dyes, flame retardants (e.g. halogenated organo-phosphoric acid compounds), inhibitors (e.g. weak acids), nucleating agents (e.g. diazo compounds), anti-oxidants, plasticizers/stabilizers (e.g. sulphonated aromatic compounds) and biocides. The amounts of these additives conventionally used would be within the purview of a person skilled in the art.

A particularly preferred class of additives which may be used herein is that of fillers. The particular advantage is that various fillers such as pulp and ground post-consumer goods (e.g. tire, reaction injection molded parts, reinforced reaction injection mold parts, off-specification personal hygiene devices, etc.) is that they can be effectively recycled in the present foamed isocyanate-based polymer with little or no compromise of aqueous fluid absorption and retention.

Once the aqueous blowing agent, catalyst, isocyanate, active hydrogen-containing compound and superabsorbent material pursuant to the present process, a reaction mixture is formed. This reaction mixture is then expanded to produce the present foamed isocyanate-based polymer. As will be apparent to those of skill in the art, the process of the present invention is useful in the production of slab foam, molded articles and the like. Thus, as will be apparent to a person skilled in the art, the manner by which expansion of the reaction mixture is effected will be dictated by the type of foam being produced. The present process may be conducted using a conventional low pressure mechanical mixhead typically used to produce slab foam) or a conventional high pressure impingement mixhead (typically used to produce molded foam).

The product of the present process is a foamed isocyanate-based polymer having a cellular structure and containing a superabsorbent material, the polymer being capable of: (i) absorbing at least about 10 times its weight of a 0.9% wt./wt. % aqueous NaCl solution maintained at a temperature of from about 20° to about 25° C., and (ii) retaining at least about 10 times its weight of absorbed NaCl solution which is bound to the superabsorbent material. Preferably the polymer is capable of: (i) absorbing at from about 10 to about 50, more preferably from about 10 to about 30, most preferably from about 10 to about 20, times its weight of a 0.9 wt./wt. % aqueous NaCl solution maintained at a temperature of from about 20° to about 25° C., and (ii) retaining from about 10 to about 50, more preferably from about 10 to about 30, most preferably from about 10 to about 20, times its weight of absorbed 0.9 wt./wt. % aqueous NaCl solution which is bound to the superabsorbent material.

The ability of the foamed isocyanate-based polymer to absorb 0.9 wt./wt. % aqueous NaCl solution or saline solution can be assessed by following "tea bag" protocol: (i) weigh empty tea bag ($W_1$); (ii) weigh test sample of foamed isocyanate-based polymer ($W_2$)—the preferred test sample is a disk having a diameter of 2 inches and a thickness of ½ inch, (iii) place test sample inside empty tea bag and seal tea bag, (iv) completely submerge sealed tea bag in the saline solution maintained at a temperature of 22°±2° C. for a period of 1 hour, (v) remove sealed tea bag from saline solution and suspend to allow gravity drainage for 5 minutes, (vi) weigh sealed tea bag ($W_3$), and (vii) calculate ($W_3$-$W_1$-$W_2$)/$W_2$ and report as the amount of 0.9 wt./wt. % aqueous NaCl solution absorbed as a multiple of the weight of the original test sample of foamed isocyanate-based polymer ($W_2$) (another way in which to report the results is as units mass of 0.9 wt./wt. % aqueous NaCl solution absorbed per unit mass of foam). The ability of the foamed isocyanate-based polymer to retain aqueous liquid can be assessed by conducting the absorption protocol and the following subsequent steps: (viii) place the sealed tea bag on a retention (drip) screen and compress the sealed tea bag containing absorbed saline solution with a compressive force of at least about 1.0 psi (more preferably at about 1.03 psi) for a period of 1 minute, (ix) weigh test sample ($W_4$), and (x) calculate ($W_4$-$W_1$-$W_2$)/$W_2$ and report as the amount of 0.9 wt./wt. % aqueous NaCl solution retained as a multiple of the weight of the original test sample of foamed isocyanate-based polymer ($W_2$) (another way in which to report the results is as units mass of 0.9 wt./wt. % aqueous NaCl solution retained per unit mass of foam). Thus, the two properties distinguish between saline which is physically and chemically bound to the foam (i.e. absorbed) and saline solution which only chemically bound to the foam (i.e. retained). For further information, see Chapter 8 of "SUPERABSORBENT POLYMERS Science and Technology", ACS Symposium Series 573, Edited by Buchholz et al. (1994), the contents of which are hereby incorporated by reference.

Another property of the present foamed isocyanate-based polymer which is useful for assessing its ability to absorb fluids is known as Absorbency Under Load or AUL. This property is discussed in more detail in U.S. Pat. No. 5,147,343, the contents of which are hereby incorporated by reference. As is known, AUL is believed to be a function of one or more of the following factors: (1) gel stiffness while swelling, (2) ability to imbibe the fluid by osmotic and internal electrostatic repulsion forces, (3) surface wettability of the foamed polymer, and (4) particle size distribution when wetted.

In the context of the present invention, it is preferred to use the following protocol for determine the AUL of the foamed isocyanate-based polymer: (i) weigh an AUL device ($W_1$)—the AUL device is a 2 inch I.D. acrylic tube having a closed, perforated end and a series of 2 inch diameter weights which are used in sufficient number to provide a predetermined applied force (e.g. 0.3 psi, 0.5 psi, 0.9 psi); (ii) weigh test sample of foamed isocyanate-based polymer ($W_2$)—the test sample is a disk having a diameter of 2 inches and a thickness of ½ inch, (iii) remove the weight(s) from the AUL device, place the test sample inside the acrylic tube of the AUL device such that the test sample is flush with the closed, perforated end of the acrylic tub, and place the weight(s) on top of the test sample, (iv) place the AUL device in a pan containing 0.9 wt./wt. % aqueous NaCl solution maintained at a temperature of 22°±2° C. for a period of 1 hour—the pan as designed should have bottom ridges or other means sufficient to allow free movement of fluid under AUL device when the latter is placed in the pan, (v) remove AUL device from pan and allow to drain for 1 minute, (vi) wipe off excess fluid from exterior of AUL device and weigh AUL device ($W_3$), and (vii) calculate ($W_3$-$W_1$-$W_2$)/$W_2$ and report as the amount of 0.9 wt./wt. % aqueous NaCl solution absorbed as the AUL, at the predetermined load, of the original test sample of foamed isocyanate-based polymer ($W_2$).

The present foamed isocyanate-based polymer has an AUL, at 0.5 psi, of at least about 5, preferably in the range of from about 5 to about 50, more preferably from about 5 to about 40, most preferably from about 5 to about 30, grams of 0.9 wt./wt. % aqueous NaCl solution absorbed per gram of foamed isocyanate-based polymer. Further, the present foamed isocyanate-based polymer has an AUL, at 0.9 psi, of at least about 5, preferably in the range of from about 5 to about 40, more preferably from about 5 to about 30, most preferably from about 5 to about 20, grams of 0.9 wt./wt. % aqueous NaCl solution absorbed per gram of foamed isocyanate-based polymer.

Thus, the retention and AUL properties of the present foamed isocyanate-based polymer are generally predictive of the retention and AUL properties which are desirable in a principal practical application of the present invention. Specifically, if the present foam product is used in the core of a diaper, the saline solution retention properties referred to above are advantageous since they are predictive of a diaper core which will absorb, inter alia, urine while mitigating against significant amounts of absorbed urine being squeezed out of the core against the skin of the child or leaking out of the diaper.

The type of superabsorbent material and the amount thereof present in the foamed isocyanate-based polymer is as discussed hereinabove in regard to the present process.

The present foamed isocyanate-based polymer has multitude of potential application. For example, the present foamed isocyanate-based polymer will is useful as the core of a personal hygiene device. However, the present foamed isocyanate-based polymer will find use in many applications in which fluid management or control is desirable, such as any of the following non-limiting examples: water bed core, gasoline tanks flood control, insect control, desiccants, horticultural applications, oil spill clean-up and the like.

Thus, as will be appreciated by those of skill in the art, the foam product of the present invention having advantageous aqueous fluid (e.g. saline) absorption, retention and AUL properties is the direct product of polymerization and expansion. In other words, the advantageous properties of the foam product of the present invention are not dependent on any specific, complicated and expensive reticulation (or other post-treatment) step such as taught by Kelly et al. discussed above. Those of skill in the art will recognize that the foam product of the present invention is not a thermally reticulated product—i.e. the foam product of the present invention is non-reticulated. Rather, the foam product of the present invention is a cellular material having an open cell structure (i.e. cells with cracked or broken membranes between cell struts as discussed above) as opposed to a skeletal matrix or structure as taught by Kelly et al.

The present foamed isocyanate-based polymer preferably has a density of from about 1.0 pcf (about 16.0 kg/m$^3$) to about 15.0 pcf (about 240 kg/m$^3$), more preferably from about 1.0 pcf (about 16.0 kg/m$^3$) to about 12.0 pcf (about 192 kg/m$^3$), even more preferably from about 1.0 pcf (about 16.0 kg/m$^3$) to about 8.0 pcf (about 128 kg/m$^3$), most preferably from about 1.5 pcf (about 16.0 kg/m$^3$) to about 5.0 pcf (about 80.1 kg/m$^3$).

Embodiments of the present invention will now be described with reference to the following Examples which should not be construed as limiting the scope of the invention. The term "pbw" used in the Examples refers to parts by weight.

In the Examples the following compounds were used:

1. DABCO-T16, a polymerization catalyst commercially available from Air Products and Chemicals, Inc.;
2. L5770, an organo-silicone surfactant available from OSi;
3. C255, an amine catalyst available from OSi;
4. Arcol 2580, a hydrophilic polyether polyol having a molecular weight of approximately 5,000 and an ethylene oxide content of approximately 75% by weight, available from Arco Chemical Company;
5. Voranol 3010, a non-hydrophilic polyether polyol having a molecular weight of approximately 3000 and an ethylene oxide content of less than about 20% by weight, commercially available from The Dow Chemical Company;
6. TDI 80, a blend of 80% by weight 2,4-toluene diisocyanate, and 20% by weight 2,6-toluene diisocyanate commercially available from Bayer Corporation under the tradename Mondur TD-80 Grade A; and
7. Sanwet IM4500, starch grafted sodium polyacrylate available from Hoechst Celanese Corporation.

EXAMPLES 1–8

In these Examples, a series of foam samples were made with varying cell sizes and varying superabsorbent material particle sizes. The general formulation used in these Examples may be found in Table 1.

TABLE 1

| Ingredient | Amount (pbw) |
|---|---|
| Arcol 2580 | 70 |
| Voranol 3010 | 30 |
| L5770 | 1.2 |
| C255 | 1.0 |

TABLE 1-continued

| Ingredient | Amount (pbw) |
|---|---|
| Water | 2.8 |
| IM4500 | 50 |
| DABCO-T16 | 0.1 |
| TDI 80 | Sufficient amount to provide an isocyanate index of about 1.05. |

Prior to use, the IM4500 was fractionated on the basis of particle size. The equipment used was a sieve holder/shaker made by W. S. Tyler of St. Catherines, Ontario, Canada (Model Rx24, Type PSS), equipped with a sequence of mesh sieves having the following sizes: 40, 60, 80 and 100. The concordance of these mesh sieves with particle size distribution of the IM4500 is reported in Table 2.

TABLE 2

| Mesh Size | Particle Size (μm) |
|---|---|
| 40 | >425 |
| 60 | >250 and <425 |
| 80 | >180 and <250 |
| 100 | <180 |

The foam samples were produced according to the following procedure.

The cell size of the resulting foam was controlled by pretreatment of the polyol mixture in a conventional manner. To produce a fine cell foam (cell size>30 cells/inch when measured pursuant to ASTM D3576-77), the polyol mixture was cooled to 5°–6° C. and carbon dioxide gas was concurrently bubbled through the mixture. To produce a coarse cell foam (cell size<30 cells/inch when measured pursuant to ASTM D3576-77), the polyol mixture was heated to approximately 30° C. for a period of at least about 3 hours.

The pretreated polyol mixture was quickly mixed with the L5770, C255 and water. The IM4500 was added to and blended with the mixture. The DABCO-T16 was added with continued mixing. Thereafter, the TDI 80 was added with mixing and the resulting reaction mixture was poured into an open container and allowed to expand to result in a polyurethane foam.

The foam was cut into appropriate sample size and subjected to saline (0.9 wt./wt. % aqueous NaCl solution) absorption, retention and AUL testing as described hereinabove. The foam cell size, IM4500 particle size, and the absorption, retention and AUL properties of the foam are reported in Table 3. For absorption, retention and AUL, each result reported in Table 3 is an average of three samples for absorption and retention, and the average of four samples for AUL.

The results reported in Table 3 demonstrate that, when the only variable in the foam is the cell size of thereof, the saline absorption and retention properties are higher for fine foam (cell size>30 cells/inch when measured pursuant to ASTM D3576-77) when compared to coarse cell foam (cell size<30 cells/inch when measured pursuant to ASTM D3576-77). Further, the results demonstrate that, when the only variable in the foam is the particle size of the superabsorbent material, the saline retention properties increase as the particle size of the superabsorbent material is increased. The most preferred foam, from the viewpoint of saline retention, is Example 1. With reference to AUL, the results demonstrate that, when the particle size of the superabsorbent material is greater than 250 μm, AUL of the foam samples improves with fine foam (cell size>30 cells/inch when measured pursuant to ASTM D3576-77) compared to coarse foam (cell size<30 cells/inch when measured pursuant to ASTM D3576-77).

TABLE 3

| Example | Cell Size[1] | Particle Size[2] | Absorption | Retention | AUL @ 0.5 psi | AUL @ 0.9 psi |
|---|---|---|---|---|---|---|
| 1 | 32 | 40 | 14.99 | 14.66 | 9.57 | 8.43 |
| 2 | 12 | 40 | 14.92 | 13.70 | 9.22 | 8.12 |
| 3 | 42 | 60 | 15.80 | 13.48 | 8.88 | 7.79 |
| 4 | 22 | 60 | 12.27 | 11.69 | 8.43 | 7.39 |
| 5 | 44 | 80 | 16.93 | 12.11 | 8.11 | 7.39 |
| 6 | 26 | 80 | 13.61 | 11.53 | 8.60 | 7.45 |
| 7 | 36 | 100 | 15.06 | 12.03 | 7.65 | 6.84 |
| 8 | 16 | 100 | 10.69 | 10.59 | 7.63 | 6.83 |

[1]Cell size of the foam sample measured pursuant to ASTM D3576-77.
[2]Mesh size of sieve use to fractionate particular IM4500 used in foam sample.

What is claimed is:

1. A foamed isocyanate-based polymer having a cellular structure and which includes a superabsorbent material, the polymer: (i) absorbing at least about 10 times its weight of a 0.9 wt./wt. % aqueous NaCl solution maintained at a temperature of from about 20° to about 25° C., and (ii) retaining at least about 10 times its weight of absorbed aqueous NaCl solution which is bound to the superabsorbent material, the cellular structure having a cell size of at least about 30 cells/inch when measured pursuant to ASTM D3576-77.

2. The foamed isocyanate-based polymer defined in claim 1, wherein the polymer is capable of: (i) absorbing from about 10 to about 50 times its weight of a 0.9 wt./wt. % aqueous NaCl solution maintained at a temperature of from about 20° to about 25° C., and (ii) retaining from about 10 to about 50 times its weight of absorbed aqueous NaCl solution which is bound to the superabsorbent material.

3. The foamed isocyanate-based polymer defined in claim 1, wherein the polymer is capable of: (i) absorbing from about 10 to about 30 times its weight of a 0.9 wt./wt. % aqueous NaCl solution maintained at a temperature of from about 20° to about 25° C., and (ii) retaining from about 10 to about 30 times its weight of absorbed aqueous NaCl solution which is bound to the superabsorbent material.

4. The foamed isocyanate-based polymer defined in claim 1, wherein the polymer is capable of: (i) absorbing from about 10 to about 20 times its weight of a 0.9 wt./wt. % aqueous NaCl solution maintained at a temperature of from about 20° to about 25° C., and (ii) retaining from about 10 to about 20 times its weight of absorbed aqueous NaCl solution which is bound to the superabsorbent material.

5. The foamed isocyanate-based polymer defined in claim 1, wherein the superabsorbent material is a synthetic polymer.

6. The foamed isocyanate-based polymer defined in claim 1, wherein the superabsorbent material is a cellulosic polymer.

7. The foamed isocyanate-based polymer defined in claim 6, wherein the cellulosic polymer is a carboxymethyl cellulose.

8. The foamed isocyanate-based polymer defined in claim 1, wherein the superabsorbent material is a polymer of at least one of an acrylic monomer and vinyl monomer.

9. The foamed isocyanate-based polymer defined in claim 1, wherein the superabsorbent material is selected from the group consisting of polyvinylpyrrolidone, sulfonated polystyrene, polysulfethyl acrylate, poly(2-hydroxyethylacrylate), polyacrylamide, polyacrylic acid, poly(acrylic acid alkali metal salt), starch modified polyacrylic acid, poly(starch modified acrylic acid alkali metal salt), hydrolyzed polyacrylonitrile, poly(hydrolyzed polyacrylonitrile alkali metal salt) and mixtures thereof.

10. The foamed isocyanate-based polymer defined in claim 1, wherein the superabsorbent material is present in an amount up to about 150 parts by weight per hundred parts by weight of active hydrogen-containing compound used to produce the foamed isocyanate-based polymer.

11. The foamed isocyanate-based polymer defined in claim 1, wherein the superabsorbent material is present in the range of from about 20 to about 80 parts by weight per hundred parts by weight of active hydrogen-containing compound used to produce the foamed isocyanate-based polymer.

12. The foamed isocyanate-based polymer defined in claim 1, wherein the superabsorbent material is present in the range of from about 25 to about 75 parts by weight per hundred parts by weight of active hydrogen-containing compound used to produce the foamed isocyanate-based polymer.

13. The foamed isocyanate-based polymer defined in claim 1, wherein the superabsorbent material is present in the range of from about 30 to about 65 parts by weight per hundred parts by weight of active hydrogen-containing compound used to produce the foamed isocyanate-based polymer.

14. A foamed polyurethane polymer which includes poly(acrylic acid alkali metal salt) in an amount in the range of from about 10 to about 65 parts by weight per hundred parts by weight of polyol used to produce the foamed polyurethane polymer, the polymer: (i) absorbing from about 10 to about 20 times its weight of a 0.9 wt/wt. % aqueous NaCl solution maintained at a temperature of from about 20° to about 25° C., and (ii) retaining from about 10 to about 20 times its weight of absorbed aqueous NaCl solution which is bound to the poly(acrylic acid alkali metal salt), the cellular structure having a cell size of at least about 30 cells/inch when measured pursuant to ASTM D3576-77.

15. A process for producing the foamed isocyanate-based polymer comprising the steps of:

contacting an isocyanate, an active hydrogen-containing compound, an aqueous blowing agent, a catalyst and a superabsorbent material, the superabsorbent material absorbing at least about 10 times its weight of a 0.9 wt./wt. % aqueous NaCl solution maintained at a temperature in the range of from about 20° to about 25° C.; and expanding the reaction mixture to produce foamed isocyanate-based polymer having a cell size of at least about 30 cells/inch when measured pursuant to ASTM D3576-77;

wherein the active hydrogen-containing compound comprises from about 10% to 100% by weight of a hydrophilic active hydrogen-containing compound and from 0 to about 90% by weight a non-hydrophilic active hydrogen-containing compound.

16. The process defined in claim 15, wherein said contacting comprises contacting a uniform mixture of the isocyanate, the active hydrogen-containing compound and the superabsorbent material with the catalyst and the aqueous blowing agent.

17. The process defined in claim 16, wherein the catalyst and the aqueous blowing agent are preblended prior to contact with the uniform mixture.

18. The process defined in claim 16, wherein the catalyst and the aqueous blowing agent are independently contacted with the uniform mixture.

19. The process defined in claim 15, wherein said contacting comprises contacting a uniform mixture of the aqueous blowing agent, the catalyst, the active hydrogen-containing compound and the superabsorbent material with the isocyanate.

20. The process defined in claim 15, wherein said contacting comprises contacting a dispersion of the active-hydrogen-containing compound and the superabsorbent material with the isocyanate, the catalyst and the aqueous blowing agent.

21. The process defined in claim 20, wherein the isocyanate, the catalyst and the aqueous blowing agent are independently contacted with the dispersion.

22. The process defined in claim 20, wherein the catalyst and the aqueous blowing agent are preblended prior to contacting with the dispersion.

23. The process defined in claim 15, wherein the active hydrogen-containing compound comprises from about 20% to about 90% by weight of a hydrophilic active hydrogen-containing compound and from about 10% to about 80% by weight a non-hydrophilic active hydrogen-containing compound.

24. The process defined in claim 15, wherein the active hydrogen-containing compound comprises from about 40% to about 90% by weight of a hydrophilic active hydrogen-containing compound and from about 10% to about 60% by weight a non-hydrophilic active hydrogen-containing compound.

25. The process defined in claim 15, wherein the active hydrogen-containing compound comprises from about 70% to about 80% by weight of a hydrophilic active hydrogen-containing compound and from about 20% to about 30% by weight a non-hydrophilic active hydrogen-containing compound.

26. The process defined in claim 15, wherein the hydrophilic active hydrogen-containing compound is a hydrophilic polyol.

27. The process defined in claim 26, wherein the hydrophilic polyol is selected from the group consisting of diols, triols and tetrols containing polyoxyalkylene groups, the polyoxyalkylene groups comprising at least 25 percent by weight of ethylene oxide.

28. The process defined in claim 15, wherein the non-hydrophilic polyol is a polyether polyol.

29. The process defined in claim 28, wherein the polyether polyol has a molecular weight in the range of from about 200 to about 20,000.

30. The process defined in claim 15, wherein the isocyanate is selected from the group comprising 2,4-toluene diisocyanate, 2,6-toluene diisocyanate and mixtures thereof.

31. The process defined in claim 15, wherein the isocyanate is selected from the group consisting essentially of (i) 2,4'-diphenylmethane diisocyanate, 4,4'-diphenylmethane diisocyanate and mixtures thereof; and (ii) mixtures of (i) with an isocyanate selected from the group comprising 2,4-toluene diisocyanate, 2,6-toluene diisocyanate and mixtures thereof.

32. A personal hygiene device having a bodily fluid absorbent layer consisting essentially of the foamed isocyanate-based polymer defined in claim 1.

33. A personal hygiene device having a bodily fluid absorbent layer consisting essentially of the foamed polyurethane polymer defined in claim 14.

* * * * *